United States Patent

Salin-Drouin

[19]

[11] Patent Number: 6,077,531
[45] Date of Patent: Jun. 20, 2000

[54] ESTRADIOL AND PROGESTERONE-BASED MEDICAMENT

[75] Inventor: Dominique Salin-Drouin, Verrieres-les-Buissons, France

[73] Assignee: Laboratoires Besins Iscovesco, Paris, France

[21] Appl. No.: 09/155,331

[22] PCT Filed: Apr. 4, 1997

[86] PCT No.: PCT/FR97/00612

§ 371 Date: Sep. 28, 1998

§ 102(e) Date: Sep. 28, 1998

[87] PCT Pub. No.: WO97/37642

PCT Pub. Date: Oct. 16, 1997

[30] Foreign Application Priority Data

Apr. 5, 1996 [FR] France ................... 96 04349

[51] Int. Cl.[7] ............... A61K 9/48; A61K 9/66; A61K 9/52; A61K 9/14; A61K 31/56
[52] U.S. Cl. .................. 424/451; 424/455; 424/457; 424/489; 514/177; 514/182
[58] Field of Search ................. 514/177, 182; 424/489, 451, 455, 457

[56] References Cited

U.S. PATENT DOCUMENTS

| 4,196,188 | 4/1980 | Besins ........................ 424/37 |
| 4,624,665 | 11/1986 | Nuwayser ................... 604/307 |
| 4,900,734 | 2/1990 | Maxson et al. ............. 514/171 |
| 5,340,584 | 8/1994 | Spicer et al. ............... 424/426 |

FOREIGN PATENT DOCUMENTS

WO 95/00125   1/1995   WIPO .

OTHER PUBLICATIONS

Chemical Abstracts, vol. 90, No. 22, May 1979.

*Primary Examiner*—Thurman K. Page
*Assistant Examiner*—Todd D Ware
*Attorney, Agent, or Firm*—Young & Thompson

[57] ABSTRACT

A medicament consisting of a biological medium-soluble capsule containing a micronised progesterone suspended in oil is disclosed, characterised in that the capsule also contains estradiol enclosed in microspheres, also suspended in oil, and which consist of one or more polymers that do not dissolve in oil but that dissolve in a biological medium.

5 Claims, 1 Drawing Sheet

ESTRADIOL AND PROGESTERONE-BASED MEDICAMENT

The present invention relates to a medicament based on estradiol and progesterone intended for the treatment of menopausal pathology.

In effect, it is known that the estrogenic deficiency which manifests itself during the period of the menopause is sometimes difficult for the feminine organism to tolerate, due in particular to the fact that it is felt not only at the level of the central nervous system, where it is responsible for outward signs of neurovegetative order, such as hot flushes, but also at the level of the osseous cartilage.

In the past, various methods of administration of estradiol have been proposed, and in particular a method of administration by the percutaneous route. As for the medicament forming the subject matter of the present invention, it can be administered by the oral route.

It is also known that, in the case of estrogenotherapy, it is usual to administer a treatment of progesterone in order to avoid in particular the risks of hyperplasia of the endometrium.

Rather than oblige the patient to take these two medicaments separately, it will be understood that it is particularly advantageous to group them together in one and the same medicament in order to allow them to be absorbed in a single dose.

Patent FR-A-2 408 345 in particular discloses medicaments based on progesterone which can be administered by the oral route. In certain of these medicaments, the progesterone is in the micronized state in suspension in a liquid constituted by oil. It is an object of the present invention to include with this medicament an appropriate quantity of estradiol.

One difficulty arises from the fact that, in order to obtain a complete dissolution of the estradiol in certain oils, and particularly in peanut oil, the quantity of oil necessary is such that the volume of the capsule of medicament is in that case such as to render absorption thereof by the user more difficult. Of course, the volume of this capsule may be reduced, but in that case the quantity of oil contained therein is insufficient to allow a total dissolution of the estradiol, with the result that the latter risks recrystallizing, which, as is well known, reduces its active character. In fact, it is perfectly well known that the size of the particles has a direct effect on the absorption of the lipophilic molecules and therefore on their activity.

U.S. Pat. No. 4,900,734 also discloses compositions intended for the treatment of menopausal pathology, containing a progesterone in the micronized state in suspension in an oil of polyunsaturated type and estradiol solubilized in this oil.

The present invention has for an object to propose a means for dispensing the estradiol and the quantity of progesterone which must normally be associated therewith, in a single capsule of small dimensions.

The present invention thus relates to a medicament constituted by a capsule soluble in a biological medium, containing a progesterone in the micronized state in suspension in oil, characterized in that the capsule also contains estradiol enclosed in microspheres also in suspension in the oil and which are constituted by at least one polymer adapted not to dissolve in oil and to dissolve in a biological medium.

In a form of embodiment of the invention, this polymer is a cellulosic polymer, particularly of the type marketed under the Trademark "KLUCEL EFEP". This polymer may also be an acrylic polymer marketed in particular under the Trademark "EUDRAGIT E100".

Applicants have established, in particularly interesting manner, as shown in the kinetic dissolution curves shown hereinbelow, that the speed of dissolution of the estradiol contained in microspheres is at least equal to, if not greater than, what it is in the normal state, i.e. in a micronized state (in other words, a state in which the particles present dimensions of the order of 5 μm). This property is particularly advantageous insofar as, up to the present time, the fact of placing an active substance in microspheres had for its effect to slow down release thereof.

Various forms of embodiment of the present invention will be described hereinafter by way of non-limiting examples, with reference to the accompanying drawings, in which.

According to the invention, microspheres of estradiol were made by means known in the prior state of the art under the name of "nebulization" (or also "spray drying"). According to this technique, particles of estradiol were introduced within a large number of microspheres made of three polymers which are different (numbered II to IV). Each of these three series of samples was subjected to a dissolution in a biological medium, or more precisely in a biological medium model commonly admitted by the specialists, and which is constituted by water to which 0.3% of sodium laurylsulfate was added.

Samples were taken during these kinetics at intervals of time of 1 minute, 30 minutes and 60 minutes, and the percentage of estradiol released was measured by a method of high-performance liquid chromatography.

The Table hereinbelow represents the quantities of estradiol released during these kinetics, respectively on a control sample constituted by estradiol in the micronized state (sample I) and the three samples II to IV mentioned hereinabove:

| Sample | % oestradiol released | | |
| --- | --- | --- | --- |
| | 1 min | 30 mins | 60 mins |
| Micronized, non-microencapsulated estradiol | | | |
| I | 34.5 | 75.9 | 80.6 |
| II | 30.9 | 72.6 | 86.7 |
| III | 29.3 | 89.0 | 90.0 |
| IV | 82 | 86 | 100 |

Sample II: 50% mixture by mass of an acrylic polymer (Registered Trademark EUDRAGIT E100) and a polyvinyl pyrrolidone (Registered Trademark KOLLIDON 30)
Sample III: %)% mixture by mass of a cellulosic derivative polymer (Registered Trademark KLUCEL EFEP) and a polyvinyl pyrrolidone (Registered Trademark KOLLIDON 30)
Sample IV: 50% mixture by mass of an acrylic polymer (Registered Trademark EUDRAGIT RL 100) and a polyvinyl pyrrolidone (Registered Trademark KOLLIDON 30)

Figure 1:
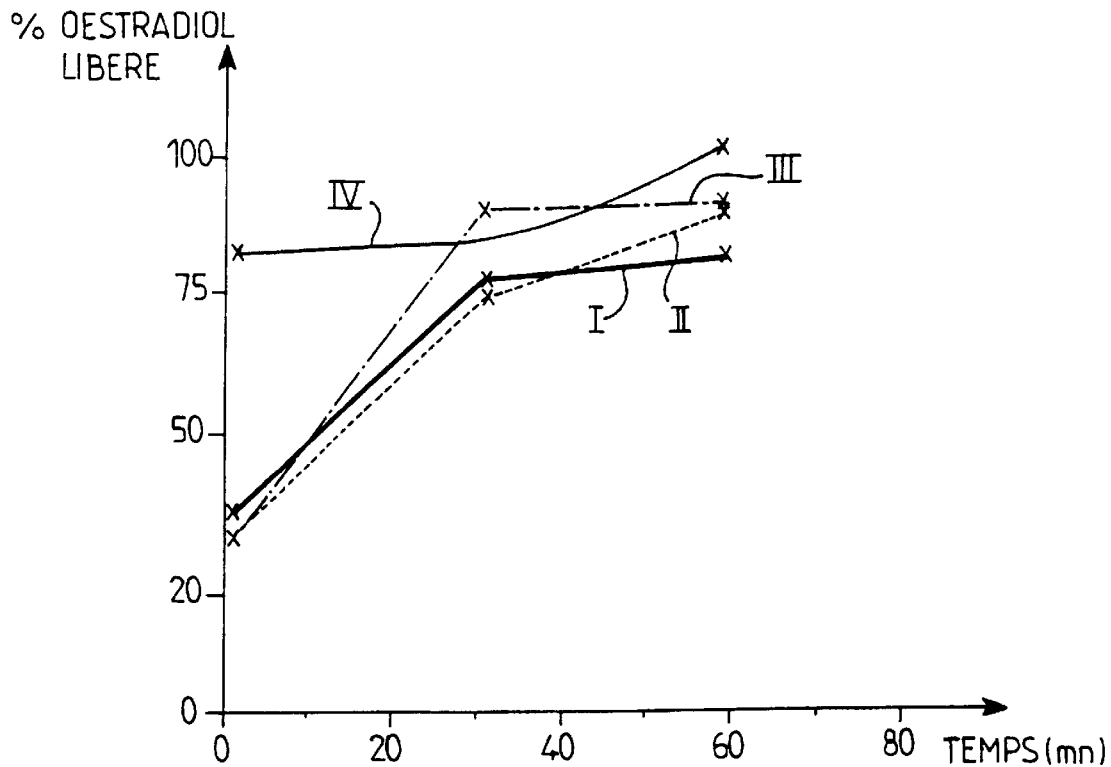
FIG. 1 is a graph showing the curves of kinetics of dissolution of estradiol respectively in the micronized state and in the state of microspheres in several polymers.

FIG. 1 represents the variation of the percentage of estradiol released as a function of the time which is characteristic of the kinetics of dissolution of these four samples.

A study of this Table, and of the corresponding curves which are associated therewith, shows that the speeds of dissolution of the estradiol enclosed in microspheres are at least equal to, and most often greater than, those of the micronized estradiol alone. This particularity is particularly surprising since it is known that it is admitted by the specialists in the art that an active substance coated in a microsphere is released less rapidly than when it is non-coated. Moreover, it is interesting as it is of such nature, in certain cases, as to promote the absorption of the active substance.

Figure 2:
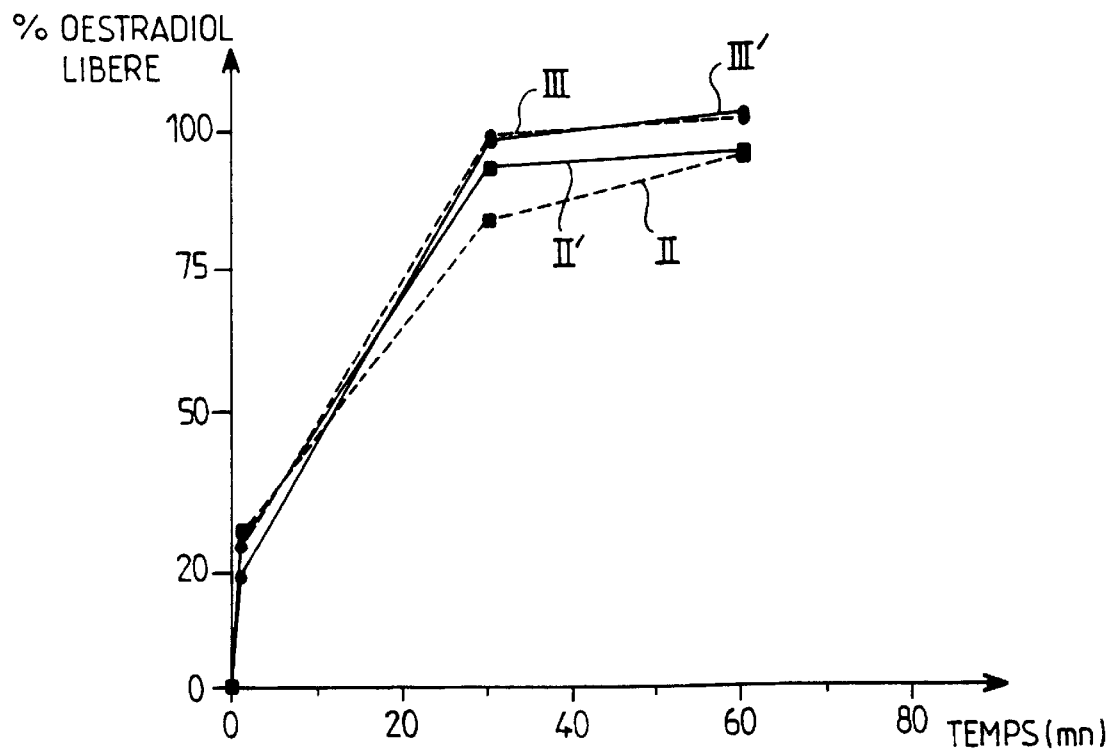
FIG. 2 is a graph showing the curves of dissolution of estradiol included in microspheres which were immerged and not immerged in oil, respectively.

Tests were then made to check whether the immersion in oil of the microspheres, constituted by different polymers enclosing particles of estradiol, had an influence on the kinetics of dissolution of these particles. To that end, kinetics were realized from, on the one hand, samples of estradiol in the form of microspheres having been immersed in a given quantity of oil and, on the other hand, from samples of estradiol in the form of microspheres not having undergone immersion in oil. Samples identical to samples II and III were used. On the graph of FIG. 2, the samples which were immersed in oil have been given the index '.

In order to realize these kinetics, the ratio of the quantities of estradiol and of oil placed in presence were respected. Thus, in the formula of medicament, 1 mg of estradiol being in contact with 149 mg of peanut oil LIPEX 101, in order to conserve this ratio, 60 mg of estradiol (or 600 mg of microspheres) were placed in the presence of 9150 mg of peanut oil LIPEX 101.

After a contact time of some hours, the oily phase which covered the capsules was eliminated by washing with hexane, then a filtration was effected. Hexane was chosen as rinsing solvent as it does not dissolve estradiol or any of the constituents which form the microsphere.

Once dried, the microspheres were recovered and the kinetics of dissolution were realized. The kinetics of dissolution made on the microspheres previously immersed in oil were then compared with the kinetics of dissolution realized on non-treated microspheres. There has been shown in FIG. 2 the variation of percentage of estradiol released as a function of the time which is characteristic of the series of samples. No really significant difference between the microspheres having undergone immersion in oil, or not, is observed in this Figure.

The present invention is particularly interesting in that it makes it posssible, from one medicament, of which some years of use have demonstrated the efficient character (namely a medicament formed by a capsule soluble in a biological medium, containing oil in which micronized particles of progesterone are suspended), to associate another active ingredient whose efficency has also been demonstrated by use, so as to constitute a two-component medicament presenting the advantages of one and the other without one of the medicaments having an intereaction on the other and while not imposing on the user patient the constraints involved in administering two separate medicaments.

What is claimed is:

1. Medicament constituted by a capsule soluble in a biological medium, containing a progesterone in the micronized state in suspension in oil, wherein the capsule also contains estradiol enclosed in microspheres also in suspension in the oil and which are constituted by at least one polymer adapted not to dissolve in the oil but to dissolve in a biological medium.

2. Medicament according to claim 1, wherein said polymer is a hydroxypropylcellulose polymer.

3. Medicament according to claim 1, wherein said polymer is a polymethacrylate polymer.

4. Medicament according to claim 1, characterized in that the polymer is a polyvinyl pyrrolidone.

5. Medicament according to claim 1 wherein the oil is peanut oil.

* * * * *